US010132895B2

(12) United States Patent
Tomoda et al.

(10) Patent No.: US 10,132,895 B2
(45) Date of Patent: Nov. 20, 2018

(54) SCAN CONDITION DETERMINING DEVICE, MAGNETIC RESONANCE IMAGING SYSTEM, SCAN CONDITION DETERMINING METHOD, AND PROGRAM (71) Applicant: GE Medical Systems Global Technology Company, LLC, Waukesha, WI (US)

(72) Inventors: Yoshihiro Tomoda, Hino (JP); Marie Uno, Taito-ku (JP)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 466 days.

(21) Appl. No.: 14/787,242

(22) PCT Filed: Apr. 24, 2014

(86) PCT No.: PCT/US2014/035303
§ 371 (c)(1),
(2) Date: Oct. 26, 2015

(87) PCT Pub. No.: WO2014/176428
PCT Pub. Date: Oct. 30, 2014

(65) Prior Publication Data
US 2016/0077179 A1    Mar. 17, 2016

(30) Foreign Application Priority Data

Apr. 25, 2013   (JP) .................................. 2013-092467

(51) Int. Cl.
G01R 33/54     (2006.01)
A61B 5/055     (2006.01)
G01R 33/56     (2006.01)

(52) U.S. Cl.
CPC ............ G01R 33/543 (2013.01); A61B 5/055 (2013.01); G01R 33/5608 (2013.01); G01R 33/546 (2013.01)

(58) Field of Classification Search
CPC .............. G01R 33/543; G01R 33/5608; G01R 33/546; A61B 5/055
(Continued)

(56) References Cited

U.S. PATENT DOCUMENTS 6,675,034 B2 *  1/2004  Sussman ........... G01R 33/56325
                                                            600/410
9,606,209 B2 *  3/2017  Ernst ................. G01R 33/56509
(Continued)

FOREIGN PATENT DOCUMENTS

CN    101669823 A    3/2010
CN    102068254      5/2011
(Continued)

OTHER PUBLICATIONS

International Search Report and Written Opinion for International Application No. PCT/US14/35303, dated Aug. 5, 2014, 16 pages.
(Continued)

Primary Examiner — Reena Aurora (57) ABSTRACT

A scan condition determining apparatus determines scan conditions in a magnetic resonance imaging system. The scan condition determining apparatus includes: a setting unit for setting an imaging range, a desired spatial resolution and a desired SN ratio; and a determining unit for determining a matrix number in a frequency encode direction and a matrix number in a phase encode direction, based on the imaging range and the desired spatial resolution set by the setting unit and determining physical parameters different from the matrix number in a frequency encode direction and a matrix number in a phase encode direction, based on the determined
(Continued)

matrix numbers, the set imaging range and the set desired SN ratio.

14 Claims, 8 Drawing Sheets

(58) Field of Classification Search
USPC .................................................. 324/314, 322
See application file for complete search history.

(56) References Cited

U.S. PATENT DOCUMENTS

| 2003/0095144 A1 | 5/2003 | Trevino et al. |
| 2010/0201360 A1 | 8/2010 | Morita |

FOREIGN PATENT DOCUMENTS

| JP | H02-224737 A | 9/1990 |
| JP | H03-207343 A | 9/1991 |
| JP | H09-262219 A | 10/1997 |
| JP | H01-062141 A | 3/1998 |
| JP | 20040201779 A | 7/2004 |
| JP | 2006-255189 A | 9/2006 |
| JP | 20010005064 A | 1/2010 |
| JP | 2011-098128 A | 5/2011 |
| JP | 2011-104041 A | 6/2011 |
| JP | 2011-229546 A | 11/2011 |
| JP | 2013-202330 A | 10/2013 |
| WO | 030021284 A1 | 3/2003 |
| WO | 20050091011 A1 | 9/2005 |
| WO | 2009/093517 A1 | 7/2009 |
| WO | 20120080904 A1 | 6/2012 |

OTHER PUBLICATIONS

Machine translation and Decision to Grant and Search issued in connection with corresponding JP Application No. 2013-092467 dated Apr. 20, 2015.

Machine translation and First Office Action and Search issued in connection with corresponding CN Application No. 201480023765.5 dated Jun. 20, 2017.

* cited by examiner

PStype:    Coil:
[FSE ▽]    [8HR Brain ▽]

Scan Plane:    Anatomy:    Contrast:    #Slices:
[Axial ▽]    [Brain ▽]    [T2 ▽]    [34 ▽]

Freq. FOV (cm):    Phase FOV (cm):    Slice Thickness (mm):    Spacing (mm):
[23.0 ▽] × [23.0 ▽]    [5.0 ▽]    [1.0 ▽]

---- 201

SNR: 5 (High)    Resolution: 5 — 0.5 (mm)
      4                   4 — 0.6 (mm)
      3 ○                3 ○ 0.7 (mm)
      2                   2 — 0.8 (mm)
      1 (Low)          1 — 0.9 (mm)

---- 202

| Freq | Phase | NEX | BW | ETL | TR | #Acq | Scan Time |
|------|-------|-----|------|-----|------|------|-----------|
| 352  | 320   | 1   | 62.5 | 22  | 4100 | 2    | 1:32      |

Actual Pixel Size: 0.65 (mm) × 0.72 (mm)
Frequency Per Pixel: 178 (Hz/pixel)

「SNR」

Low  Average of SNR:1.19
1
   0.00-0.30: 00
   0.30-0.60: 000000000000000000
2
   0.60-0.90: 0000000000000000000000000000
   0.90-1.20: 000000000000000000000000000000000000000
3
   1.20-1.50: 0000000000000000000000000
   1.50-1.80: 000000
4
   1.80-2.10: 000
   2.10-2.40: 000
5
   2.40-2.70: 0000000000
   2.70-3.00: 0
   3.00-3.30:
High

SCAN CONDITION DETERMINING DEVICE, MAGNETIC RESONANCE IMAGING SYSTEM, SCAN CONDITION DETERMINING METHOD, AND PROGRAM

CROSS-REFERENCE TO RELATED APPLICATIONS

This is a national stage application under 35 U.S.C. § 371(c) of prior filed, co-pending PCT Patent Application No. PCT/US2014/035303, filed on Apr. 24, 2014, which claims priority to Japan Patent Application No. 2013-092467, filed on Apr. 25, 2013. The aforementioned applications are herein incorporated in their entirety by reference.

BACKGROUND

The present invention relates to a technology which optimizes scan conditions in a magnetic resonance imaging system.

Parameters to which a general operator pays attentions when adjustments in scan conditions are made in a magnetic resonance imaging system, include an SN ratio, a spatial resolution, a scan time, contrast, an imaging range and the like. The imaging range is also called coverage. The operator adjusts a plurality of physical parameters in such a manner that these parameters become desired settings respectively (refer to a patent document 1 and an abstract).

There are, however, many physical parameters that affect the parameters to which the operator pays attention. Further, the way of affecting the parameters is so complicated. Therefore, there are things that the operator has to determine a number of physical parameters through a trial and error process in order to bring the parameters to which the operator himself/herself pays attention, to desired settings, thus causing a large burden on the operator.

With the foregoing in view, there has been a demand for a technology capable of more conveniently performing the optimization of scan conditions in the magnetic resonance imaging system.

SUMMARY

The invention of a first aspect provides a scan condition determining device which determines scan conditions in a magnetic resonance imaging system, which includes setting means for setting an imaging range, a desired spatial resolution and a desired SN ratio, and determining means for determining a matrix number in a frequency encode direction and a matrix number in a phase encode direction, based on the imaging range and the desired spatial resolution set by the setting means and determining physical parameters different from the matrix number in the frequency encode direction and the matrix number in the phase encode direction, based on the determined matrix numbers, the set imaging range and the set desired SN ratio.

Incidentally, the "physical parameters" are considered to include, for example, a matrix number in a frequency encode direction "Frequency", a matrix number in a phase encode direction "Phase", a band width "BW", the number of additions "NEX", an echo train length "ETL", a repetition time "TR", the number of measurements "#Acq", an inversion time "TI", an echo time "TE" and the like.

Further, the "matrix number" means the number of pixels.

The invention of a second aspect provides the scan condition determining device according to the first aspect, in which the setting means prepares a plurality of spatial resolutions as choices according to set contents of an imaging region and/or a scan method and sets a selected spatial resolution as the desired spatial resolution.

The invention of a third aspect provides the scan condition determining device according to the second aspect, in which the choices of the spatial resolutions are determined based on statistics of scan conditions set in the past.

The invention of a fourth aspect provides the scan condition determining device according to any one of the first through third aspects, in which the setting means prepares a plurality of SN ratios as choices according to set contents of an imaging region and/or a scan method and sets a selected SN ratio as the desired SN ratio.

The invention of a fifth aspect provides the scan condition determining device according to the fourth aspect, in which the choices of the SN ratios are determined based on statistics of scan conditions set in the past.

The invention of a sixth aspect provides the scan condition determining device according to any one of the first through fifth aspects, in which the determining means determines the matrix number in the frequency encode direction and the matrix number in the phase encode direction in such a manner that an FOV area determined by the imaging range, the matrix number in the frequency encode direction and the matrix number in the phase encode direction, and the desired spatial resolution satisfy an equation which prescribes a mutual relationship between these.

The invention of a seventh aspect provides the scan condition determining device according to any one of the first through sixth aspects, in which the determining means determines the matrix number in the frequency encode direction and the matrix number in the phase encode direction in such a manner that a value obtained by subtracting the matrix number in the phase encode direction from the matrix number in the frequency encode direction becomes less than a predetermined value.

The invention of an eighth aspect provides the scan condition determining device according to the seventh aspect, in which the predetermined value is determined based on statistics of scan conditions set in the past.

The invention of a ninth aspect provides the scan condition determining device according to any one of the first through eighth aspects, in which the physical parameters include at least one of a band width and the number of additions.

The invention of a tenth aspect provides the scan condition determining device according to the ninth aspect, in which the determining means prepares a plurality of combinations each based on a band width and the number of additions as choices according to set contents of an imaging region and/or a scan method, and determines the band width and the number of additions by adopting a combination in which an SN ratio estimated upon adoption of each of the plurality of combinations among the plurality of combinations becomes more than the desired SN ratio and in which a scan time estimated upon the combination adoption among the plurality of combinations becomes minimal.

The invention of an eleventh aspect provides the scan condition determining device according to the tenth aspect, in which the choices of the plurality of combinations are determined based on statistics of scan conditions set in the past.

The invention of a twelfth aspect provides the scan condition determining device according to any one of the ninth through eleventh aspects, in which the determining means determines the band width and the number of additions and further determines an echo train length, based on the determined matrix number in the frequency encode direction, matrix number in the phase encode direction, band width and number of additions, and set contents of a data acquiring method.

The invention of a thirteenth aspect provides a magnetic resonance imaging system including a scan condition determining device according to any one of the first through twelfth aspects.

The invention of a fourteenth aspect provides a scan condition determining method for determining scan conditions in a magnetic resonance imaging system, which includes the steps of setting an imaging range, a desired spatial resolution and a desired SN ratio, and determining a matrix number in a frequency encode direction and a matrix number in a phase encode direction, based on the imaging range and the desired spatial resolution set by the setting step and determining physical parameters different from the matrix number in the frequency encode direction and the matrix number in the phase encode direction, based on the determined matrix numbers, the set imaging range and the set desired SN ratio.

The invention of a fifteenth aspect provides the scan condition determining method according to the fourteenth aspect, in which the physical parameters include at least one of a band width and the number of additions.

The invention of a sixteenth aspect provides the scan condition determining method according to the fifteenth aspect, in which in the determining step, the band width and the number of additions are determined and further an echo train length is determined based on the determined matrix number in the frequency encode direction, matrix number in the phase encode direction, band width and number of additions, and set contents of a data acquiring method.

The invention of a seventeenth aspect provides a program for causing a computer to function as a scan condition determining device according to any one of the first through twelfth aspects.

According to the invention of the above aspects, with the above-described configuration, it is possible to begin with parameters to which an operator pays attention and to automatically determine individual physical parameters so as to satisfy the parameters, thereby making it possible to more conveniently perform the optimization of scan conditions in a magnetic resonance imaging system.

BRIEF DESCRIPTION OF DRAWINGS

Further objects and advantages of the present invention will be apparent from the following description of the preferred embodiments of the invention as illustrated in the accompanying drawings.

DETAILED DESCRIPTION

Figure 1:
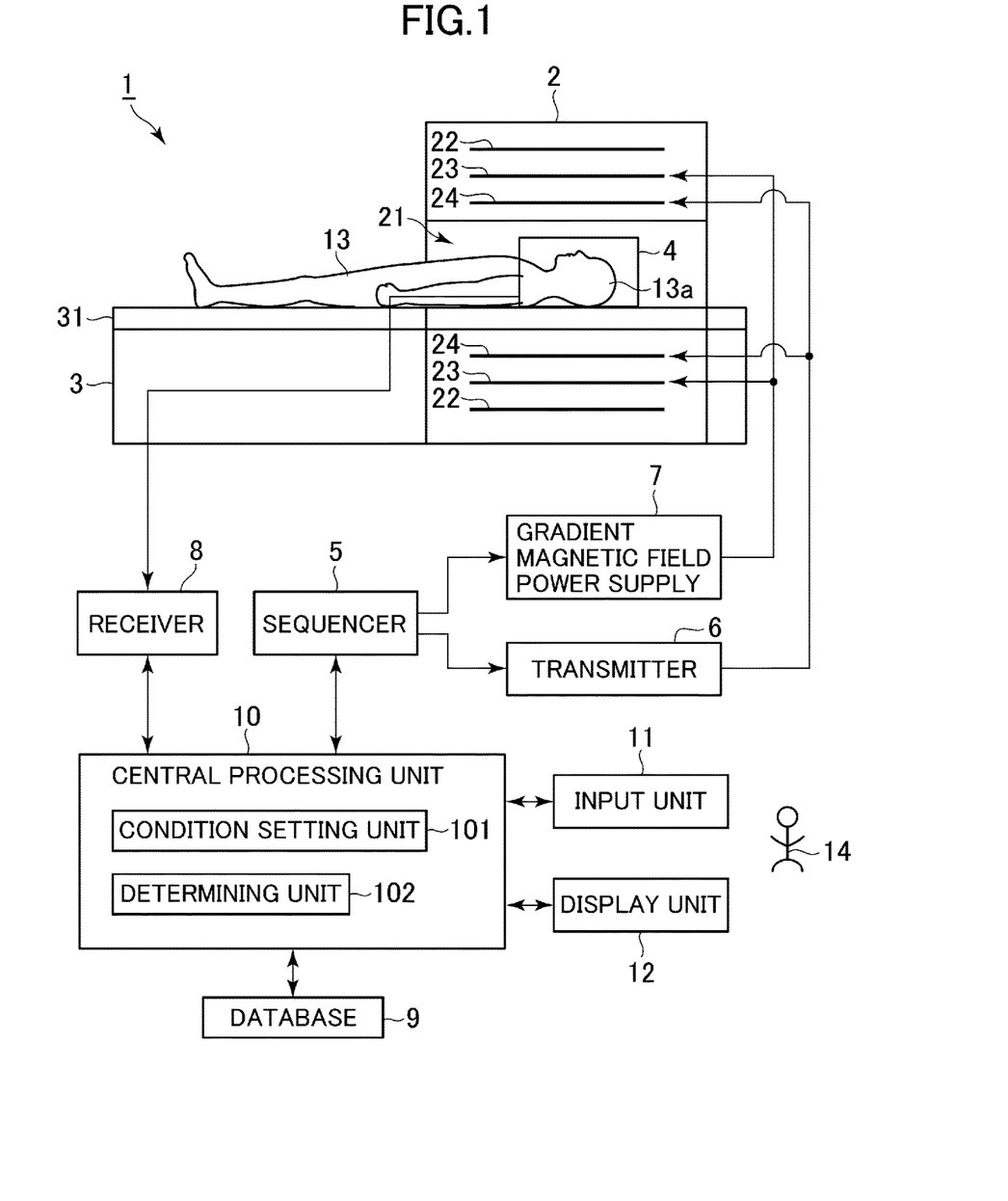
FIG. 1 is a schematic diagram of a magnetic resonance imaging system according to the present embodiment.

FIG. 1 is a schematic diagram of a magnetic resonance imaging system (hereinafter called MRI system) according to the present embodiment The MRI system 1 has a magnetic field generator 2, a table 3, a receiving coil 4 and the like.

The magnetic field generator 2 has a bore 21 in which a subject 13 is accommodated, a superconductive coil 22, a gradient coil 23 and a transmitting coil 24. The superconductive coil 22 applies a static magnetic field B0 to the bore 21. The gradient coil 23 applies a gradient magnetic field to the bore 21. The transmitting coil 24 transmits an RF pulse (Radio Frequency pulse) to the bore 21. Incidentally, a permanent magnet may be used instead of the superconductive coil 22.

The table 3 has a cradle 31 for conveying the subject 13. The subject 13 is conveyed to the bore 21 by the cradle 31.

The receiving coil 4 is attached close to an imaging region 13a of the subject 13 and receives magnetic resonance signals from the imaging region 13a.

The MRI system 1 further has a sequencer 5, a transmitter 6, a gradient magnetic field power supply 7, a receiver 8, a database 9, a central processing unit 10, an input device 11 and a display device 12.

Under the control of the central processing unit 10, the sequencer 5 transmits information (center frequency, band width or the like) of RF pulses to the transmitter 6 and sends information (the intensity of a gradient magnetic field or the like) of the gradient magnetic field to the gradient magnetic field power supply 7.

The transmitter 6 drives the transmitting coil 24, based on the information transmitted from the sequencer 5.

The gradient magnetic field power supply 7 drives the gradient coil 23, based on the information sent from the sequencer 5.

The receiver 8 signal-processes each magnetic resonance signal received by the receiving coil 4 and transmits it to the central processing unit 10.

The database 9 stores data of a reconstructed image, scan conditions, a program and the like therein.

The central processing unit 10 controls the operations of respective parts of the MRI system 1 so as to realize various operations of the MRI system 1 such as transmission of information necessary for the sequencer 5 and the display device 12, reconstruction of an image based on each signal received from the receiver 8, etc. Incidentally, the central processing unit 10 is configured by, for example, a computer and executes a predetermined program to thereby function as the device concerned. Further, the central processing unit 10 automatically performs the optimization of parameters that determine scan conditions. Here, the optimization of the parameters is to determine parameters for acquiring in a possible short scan time, scan data necessary to generate an MR image having image quality (image quality appropriate for an image diagnosis in most cases) that an operator 14 desires.

The central processing unit 10 has a condition setting part 101 and a determining part 102 for automatically performing the optimization of parameters for determining scan conditions.

The condition setting part 101 sets the values of parameters to which the operator 14 pays attention and selects a choice thereof. The parameters set herein include a parameter for prescribing an imaging range (coverage), a parameter indicative of image quality that the operator 14 desires, etc.

The determining part 102 determines the values of other individual parameters, based on the values of the parameters set by the condition setting part 101 and the choice selected thereby.

The input device 11 inputs various instructions to the central processing unit 10 in response to the manipulation of the operator 14. The display device 11 displays various information thereon.

Thus, a description will be made of processing by the MRI system 1 when the scan conditions are determined.

In the present example, the processing in the MRI system 1 when the scan conditions are determined includes a process of automatically performing the optimization of parameters for determining scan conditions.

Figure 2:
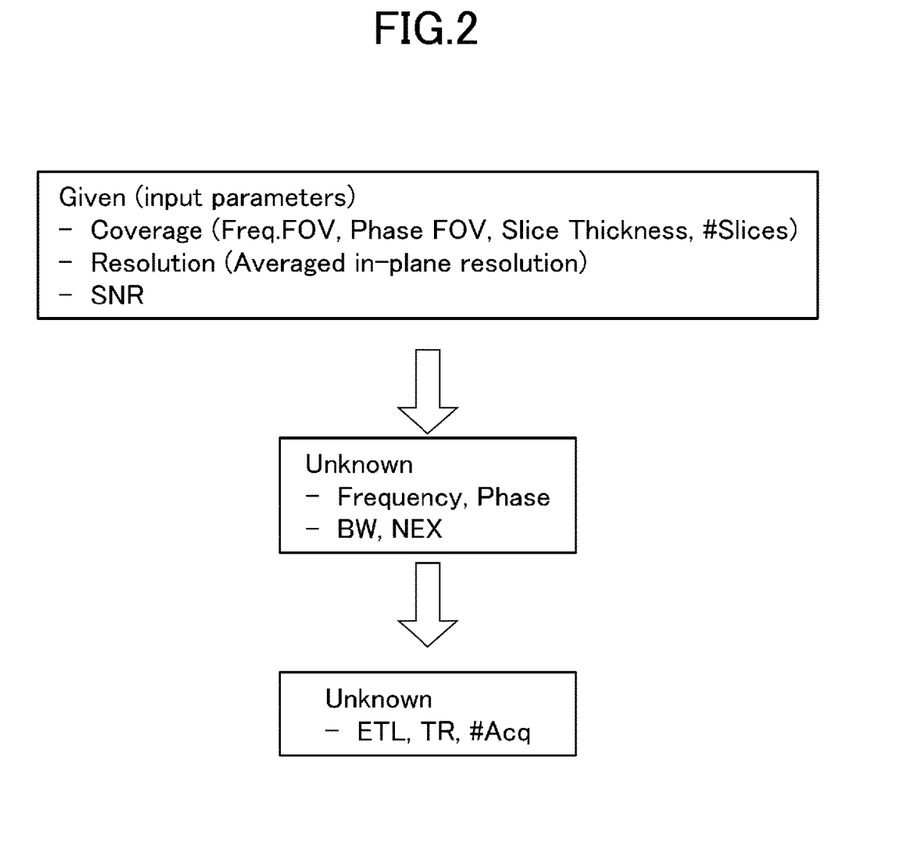
FIG. 2 is a conceptual diagram of a process of automatically performing the optimization of parameters for determining scan conditions.

FIG. 2 is a conceptual diagram of the process of automatically performing the optimization of the parameters for determining the scan conditions.

In the present example, as shown in FIG. 2, the values of a matrix number in a frequency encode direction "Frequency" and a matrix number in a phase encode direction "Phase", a band width "BW" and the number of additions "NEX" in an image to be generated are determined based on the set contents of FOV in the frequency encode direction "Freq. FOV", FOV in the phase encode direction "Phase FOV", a slice thickness "Slice Thickness" (the plus (+) number of slices "+Slices"), a desired spatial resolution "Resolution", and a desired SN ratio "SNR". Further, the values of an echo train length "ETL", a repetition time "TR" and the number of measurements "#Acq" are determined.

Figure 3:
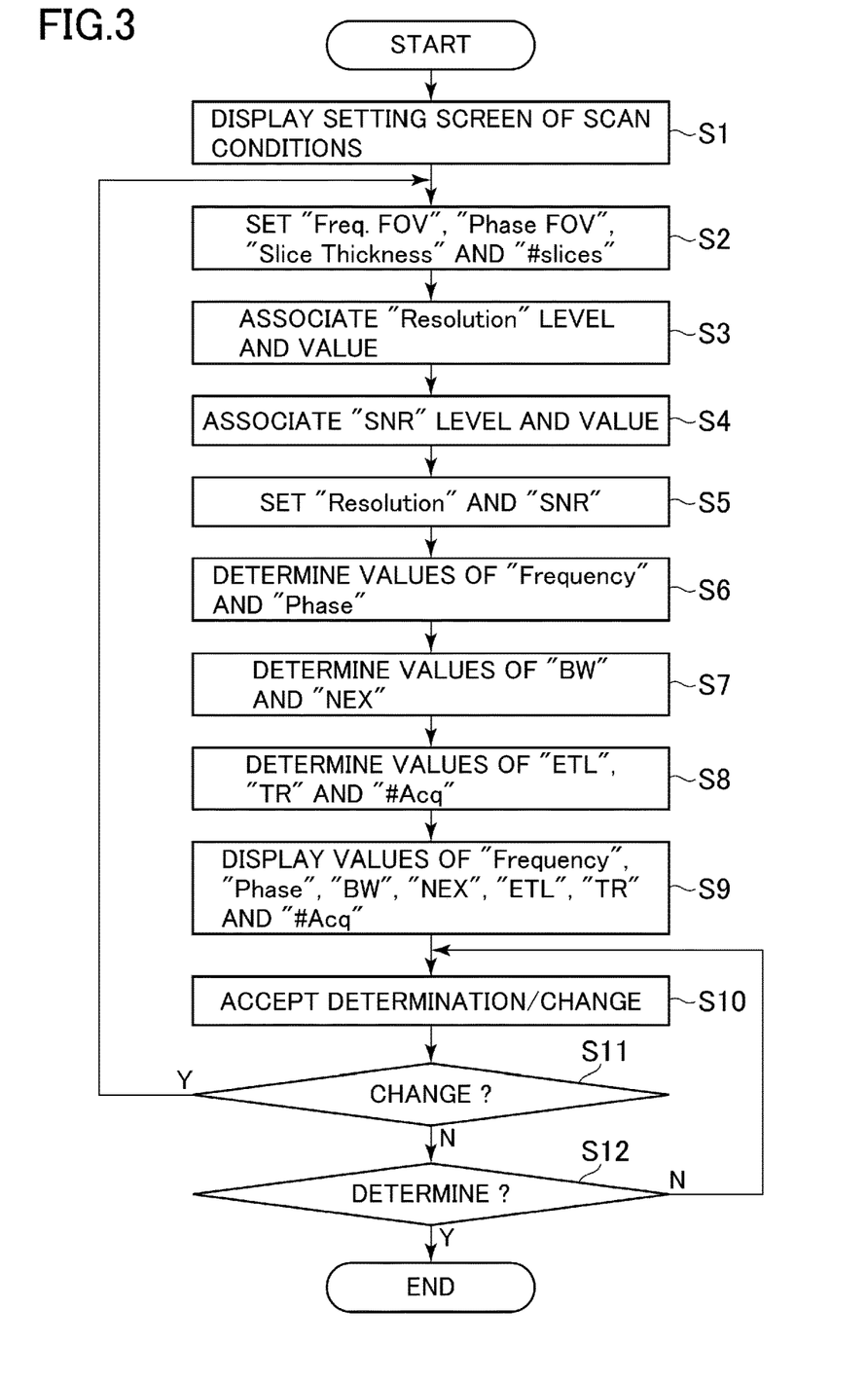
FIG. 3 is a diagram showing the flow of processing in the MRI (Magnetic Resonance Imaging) system when scan conditions are determined.

FIG. 3 is a diagram showing the flow of processing in the MRI system 1 when scan conditions are determined.

At step S1, the operator 14 manipulates the input device 11 to cause the display device 12 to display a screen for determining scan conditions. The displayed screen is a screen for automatically optimizing and determining some of parameters for determining the scan conditions. Incidentally, a screen for manually setting almost all of parameters for determining scan conditions can also be actually displayed, but the description of this screen will be omitted herein.

Figure 4:
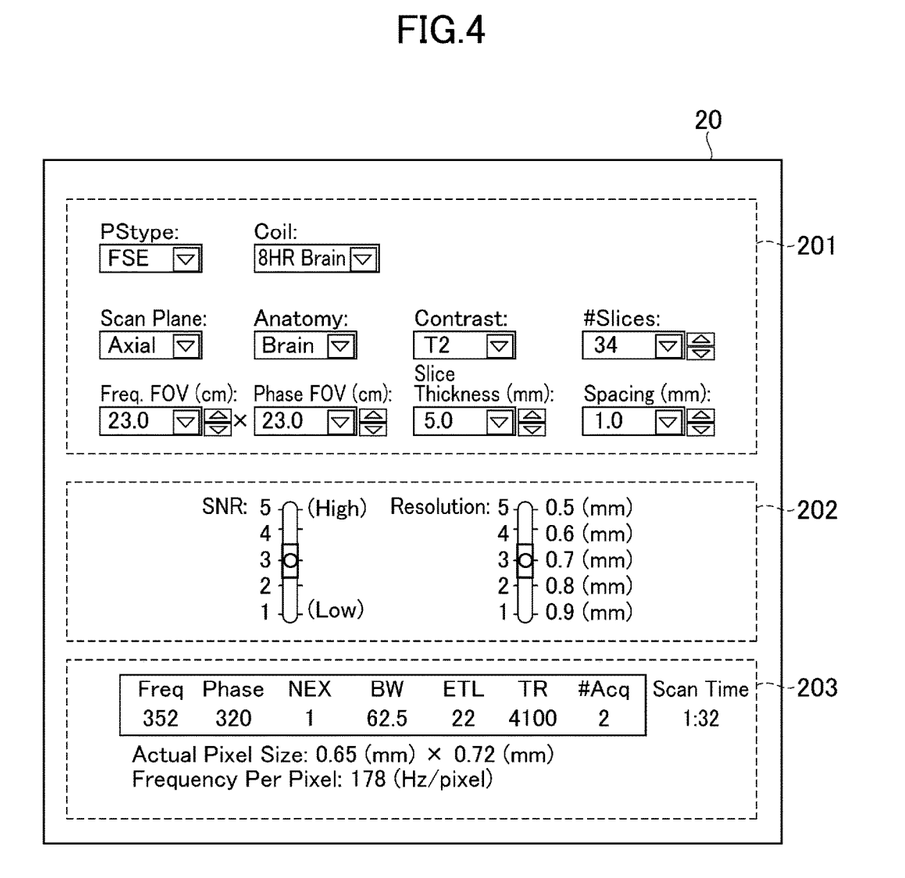
FIG. 4 is a diagram illustrating one example of a display screen for determining scan conditions.

FIG. 4 is a diagram showing one example of a display screen for determining scan conditions.

As shown in FIG. 4, various parameters are displayed on the display screen 20 for determining the scan conditions. Incidentally, parameters other than the parameters shown in FIG. 4 may be actually displayed, but the description of those parameters will be omitted herein for convenience.

Parameters which are some of the parameters for determining the scan conditions and set by the operator 14 are being displayed in an upper portion 201 of the display screen. Described specifically, there are displayed a data acquiring method (pulse sequence) "PStype", a receiving coil "Coil", an imaging section "Scan Plane", an imaging region "Anatomy", contrast (acquired image) "Contrast", the number of slices "#Slices", FOV in a frequency encode direction "Freq. FOV", FOV in a phase encode direction "Phase FOV", a slice thickness "Slice Thickness" and a slice interval "Spacing".

The operator 14 is able to arbitrarily set/change these parameters manually. Incidentally, any initial values may first be set to these parameters.

In the example shown in FIG. 4, "FSE (Fast Spin Echo)", "8 HR Brain", "Axial", "Brain", "T2", "34", "23.0", "23.0", "5.0" and "1.0" have respectively been set to "PStype", "Coil", "Scan Plane", "Anatomy", "Contrast", "#Slices", "Freq. FOV", "Phase FOV", "Slice Thickness" and "Spacing".

There have been displayed in a central portion 202 of the display screen, parameters which are parameters for setting image quality that the operator 14 desires and used as criteria when others of the parameters for determining the scan conditions are automatically optimized. Specifically, an SN ratio "SNR" and a spatial resolution "Resolution" have been displayed therein.

Here, the SN ratio "SNR" means an SN ratio that the operator 14 desires in scan data. The operator 14 is able to select and set as an SN ratio level, a desired SN ratio out of choices based on a plurality of SN ratios by switching a selector switch. In the present example, the selector switch is a slider bar (slider & bar). As the plural SN ratio levels, five stages of "1 (Low)" through "5(High)" are prepared in the present example. The plural SN ratio levels are respectively associated with a plurality of concrete SN ratios. The correspondence relationship between the SN ratio levels and the SN ratios is determined based on the set contents of the imaging region "Anatomy", the scan method (data acquiring method (pulse sequence) "PStype" and the contrast (acquired image)"Contrast". A method of determining the correspondence relationship between the SN ratio levels and concrete SN ratios will be described in detail later. Incidentally, any initial value is first set as each of the SN ratio levels. In the example of FIG. 14, "3" have been set as the initial value for the SN ratio level.

The spatial resolution "Resolution" means an average spatial resolution that the operator 14 desires in a generated image. The operator 14 is capable of selecting and setting as a spatial resolution level, a desired spatial resolution out of choices based on a plurality of spatial resolutions by switching a selector switch. Five stages of "1(Low)" through "5(High)" have been prepared as the spatial resolution levels. The plural spatial resolution levels have respectively been associated with a plurality of concrete spatial resolutions. The concrete spatial resolutions have been displayed in association with the respective spatial resolution levels. In the example of FIG. 4, "0.9 (mm)", "0.8 (mm)", "0.7 (mm)", "0.6 (mm)" and "0.5 (mm)" have respectively been associated with spatial resolution levels "1", "2", "3", "4" and "5". The correspondence relationship between the plural spatial resolution levels and the plural spatial resolutions is determined based on the set contents of the imaging region "Anatomy", the scan method (data acquiring method (pulse sequence) "PStype" and the contrast (acquired image)"Contrast". A method of determining the correspondence relationship between the spatial resolution levels and concrete spatial resolutions will be described in detail later. Incidentally, any initial value has first been set as each of the spatial resolution levels. In the example of FIG. 4, "3" have been set as the initial value for the spatial resolution level.

The remaining parameters which are the parameters for determining the scan conditions and are automatically set based on the parameters set by the operator 14, are being displayed in a lower portion 203 of the display screen.

Described concretely, there are displayed a matrix number in a frequency encode direction "Frequency", a matrix number in a phase encode direction "Phase", the number of additions "NEX", a band width "BW", an echo train length "ETL", a repetition time "TR" of the pulse sequence, the number of measurements "#Acq", and the like in a generated image. Incidentally, since the parameters for determining the scan conditions slightly differ depending on the set contents of the data acquiring method "PStype", the parameters displayed herein slightly change depending on their set contents.

At step S2, the operator 14 sets in the upper portion 201 of the display screen, the parameters ("Freq. FOV", "Phase FOV", "Slice Thickness", "#Slices", etc.) set by the operator 14, of the parameters for determining the scan conditions by inputting values and selecting choices. The condition setting part 101 sets these parameters according to the manipulation of the operator 14.

At step S3, the condition setting part 101 associates concrete spatial resolutions with a plurality of levels each prepared as a choice for the spatial resolution "Resolution".

A range suitable for the setting of the spatial resolution is generally determined according to the settings of the imaging region "Anatomy" and the scan method (data acquiring method "PStype" and contrast "Contrast"). The range can theoretically or experimentally be determined. Thus, specifically, for example, spatial resolutions respectively allocated to a plurality of spatial resolution levels are determined in advance for every settable combination of the imaging region "PStype" and the scan method (data acquiring method "PStype" and contrast "Contrast"). They are prepared in a table. Then, referring to the table, the spatial resolutions corresponding to the actual set contents of the imaging region "PStype" and the scan method (data acquiring method "PStype" and contrast "Contrast") are read and assigned to the plural spatial resolution levels respectively.

A spatial resolution determining method based on statistics will now be described as one example of a method for determining the spatial resolutions respectively assigned to the spatial resolution levels for every settable combination of the imaging region "Anatomy" and the scan method (data acquiring method "PStype" and contrast "Contrast"). This method is used to determine the suitable assignment of spatial resolutions by utilizing as teacher data, a number of scan conditions actually set in the past.

Figure 5:
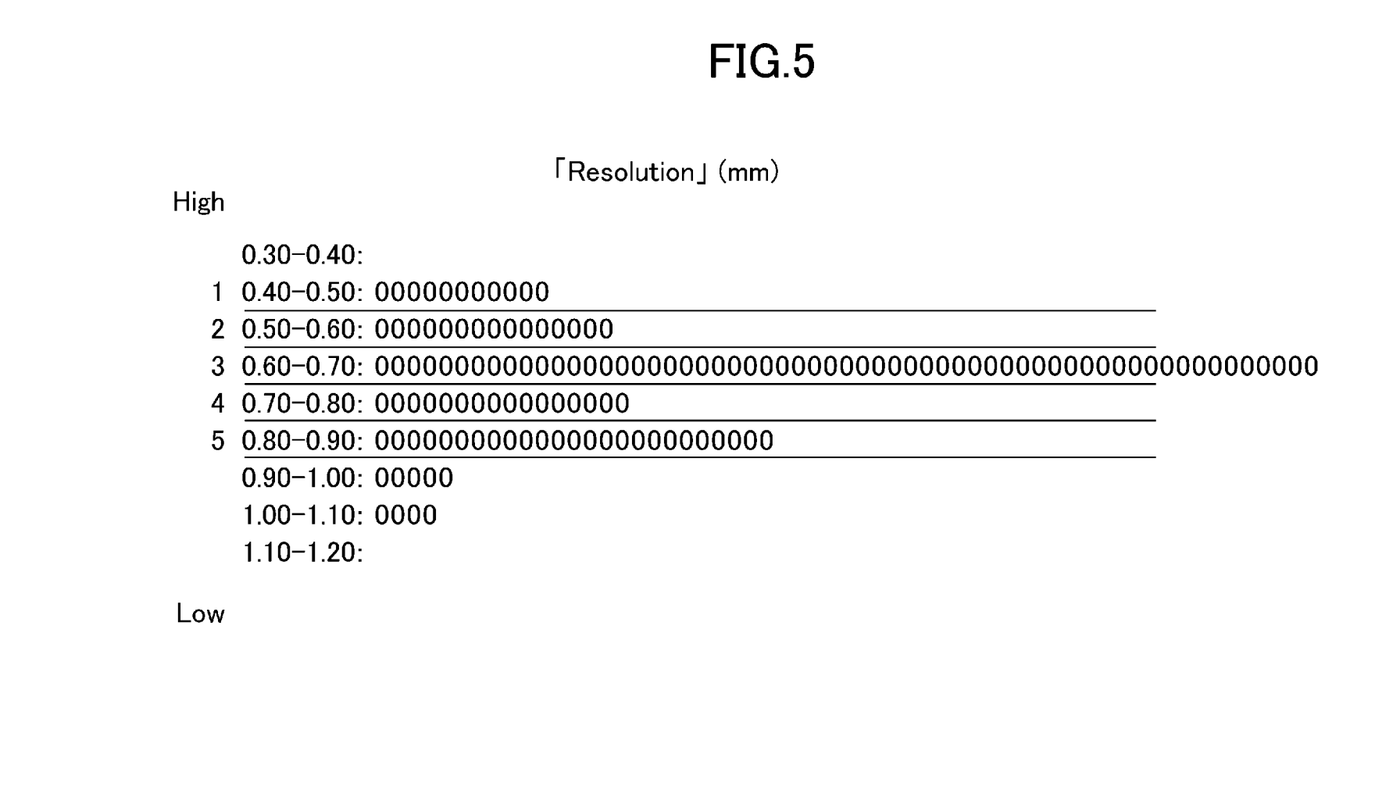
FIG. 5 is an example of a histogram of spatial resolutions in a number of scan conditions actually set in the past.

FIG. 5 is an example of a histogram of spatial resolutions in a number of scan conditions actually set in the past. In the histogram of FIG. 5, the vertical axis indicates the spatial resolution, and the horizontal axis indicates the frequency, respectively. The histogram means that the more the number of round symbols increases, the higher the frequency. The width of each bin in the histogram has been adjusted in such a manner that the distribution shape of the frequency often appears and the assignment of the SN ratios is facilitated. In the example of FIG. 5, the set contents of the imaging region "Anatomy" and the scan method (data acquiring method "PStype" and contrast "Contrast") have been narrowed down under the condition of being "Brain", "FSE" and "T2". In this histogram, most of the spatial resolutions fall within a scope from a range of "0.40 to 0.50 (mm)" to a range of "0.80 to 0.90 (mm)". A range highest in frequency, i.e., most popular is "0.60 to 0.70 (mm)". Thus, the assignment of spatial resolutions to a plurality of spatial resolution levels where, for example, the set contents of the imaging region "Anatomy" and the scan method (data acquiring method "PStype" and contrast "Contrast") are "Brain", "FSE" and "T2" respectively is determined as follows. First, the spatial resolution level "3" located in the center of the spatial resolution levels is assigned "0.70 (mm)" corresponding to the upper limit value of the range highest in frequency. Such spatial resolutions as to assign "0.6 (mm)" to the spatial resolution level "2", "0.50 (mm)" to the spatial resolution level "1", "0.80 (mm)" to the spatial resolution level "4" and "0.90 (mm)" to the spatial resolution level "5" respectively are determined. A determination similar to this is performed for each settable combination of the imaging region "Anatomy" and the scan method (data acquiring method "PStype" and contrast "Contrast"). Incidentally, the above assignment is not limited to the upper limit value of the range, but may be its center value, its lower limit value or the like.

At step S4, the condition setting part 101 associates concrete SN ratios with a plurality of levels prepared as choices of SN ratios "SNR" respectively.

A range suitable for the setting of each SN ratio is generally determined depending on the settings of the imaging region "Anatomy" and the scan method (data acquiring method "PStype" and contrast "Contrast") and can theoretically or experimentally be determined. Thus, specifically, for example, SN ratios respectively allocated to a plurality of SN ratio levels are determined in advance for every settable combination of the imaging region "Anatomy" and the scan method (data acquiring method "PStype" and contrast "Contrast"). They are prepared in a table. Then, referring to the table, the SN ratios corresponding to the actual set contents of the imaging region "Anatomy" and the scan method (data acquiring method "PStype" and contrast "Contrast") are assigned to a plurality of SN ratio levels.

An SN ratio determining method based on statistics will now be described as one example of a method for determining the SN ratios respectively assigned to the SN ratio levels for every settable combination of the imaging region "Anatomy" and the scan method (data acquiring method "PStype" and contrast "Contrast"). This method is used to determine the suitable assignment of SN ratios by utilizing as teacher data, a number of scan conditions actually set in the past. Incidentally, this combination may be taken as a combination further including a receiving coil "Coil".

Figure 6:
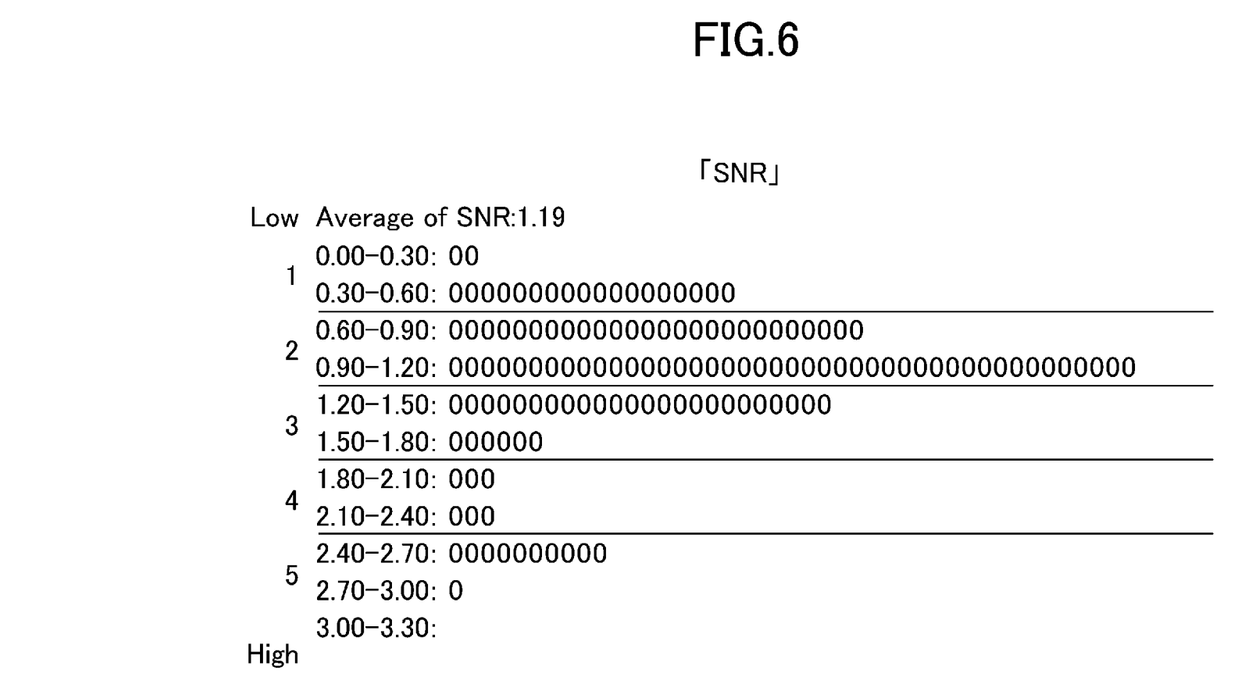
FIG. 6 is an example of a histogram of SN ratios in a number of scan conditions actually set in the past.

FIG. 6 is an example of a histogram of SN ratios in a number of scan conditions actually set in the past. In the histogram of FIG. 6, the vertical axis indicates the SN ratio, and the horizontal axis indicates the frequency. The histogram means that the more the number of round symbols increases, the higher the frequency. The width of each bin in the histogram has been adjusted in such a manner that the distribution shape of the frequency often appears and the assignment of the SN ratios is facilitated. The example of FIG. 6 shows that the set contents of the imaging region "Anatomy" and the scan method (data acquiring method "PStype" and contrast "Contrast") have been narrowed down under the condition of being "Brain", "FSE" and "T2". In this histogram, the SN ratios have widely been adopted over the scope from a range of "0.00 to 0.30" to a range of "2.70 to 3.00". Thus, the assignment of SN ratios to a plurality of SN ratio levels where, for example, the set contents of the imaging region "Anatomy" and the scan method (data acquiring method "PStype" and contrast "Contrast") are "Brain", "FSE" and "T2" respectively is determined as follows. "0.00" through "3.00" is divided into five equal parts, which in turn are assigned to SN ratio levels "1" through "5" respectively. That is, in the present example, such SN ratios as to assign "0.30" to the SN ratio level "1", "0.90" to the SN ratio level "2", "1.50" to the SN ratio level "3", "2.10" to the SN ratio level "4" and "2.70" to the SN ratio level "5" respectively are determined. A determination similar to this is performed for each settable combination of the imaging region "Anatomy" and the scan method (data acquiring method "PStype" and contrast "Contrast").

At step S5, the operator 14 sets parameters ("Resolution" and "SNR") indicative of his/her own desired image quality in the central portion 202 of the display screen. The condition setting part 101 performs the setting of these parameters according to the manipulation of the operator 14.

At step S6, the determining part 102 determines the values of the matrix number in the frequency encode direction "Frequency" and the matrix number in the phase encode direction "phase", based on the set contents of the spatial resolution level "Resolution", FOV in the frequency encode direction "Freq. FOV" and FOV in the phase encode direction "Phase FOV".

Described specifically, for example, the values of "Frequency" and "Phase" are determined to satisfy an equation (1) indicative of a physical relation between mutual "Resolution", "Freq. FOV", "Phase FOV", "Frequency" and "Phase", an equation (2) indicative of a condition for preventing a difference between vertical and horizontal resolutions in a generated image from increasing and becoming an unnatural image, and an equation (3) indicative of a condition based on a restriction on the design specification of the magnetic resonance imaging system 1. Incidentally, a threshold T in the equation (2) can theoretically or experimentally be determined.

SQR(("Freq. *FOV*"×"Phase *FOV*")/("Frequency"× "Phase"))="Resolution"(Spatial resolution)    (1)

"Frequency"−"Phase"≤*T*    (2)

"Frequency"=32×*n*, "Phase"=32×*m* (where *n* and *m*: natural numbers)    (3)

A threshold determining method based on statistics will now be described as one example of a method of determining the threshold T in the equation (2). This method is used to determine an appropriate threshold by using a number of scan conditions actually set in the past as teacher data.

Figure 7:
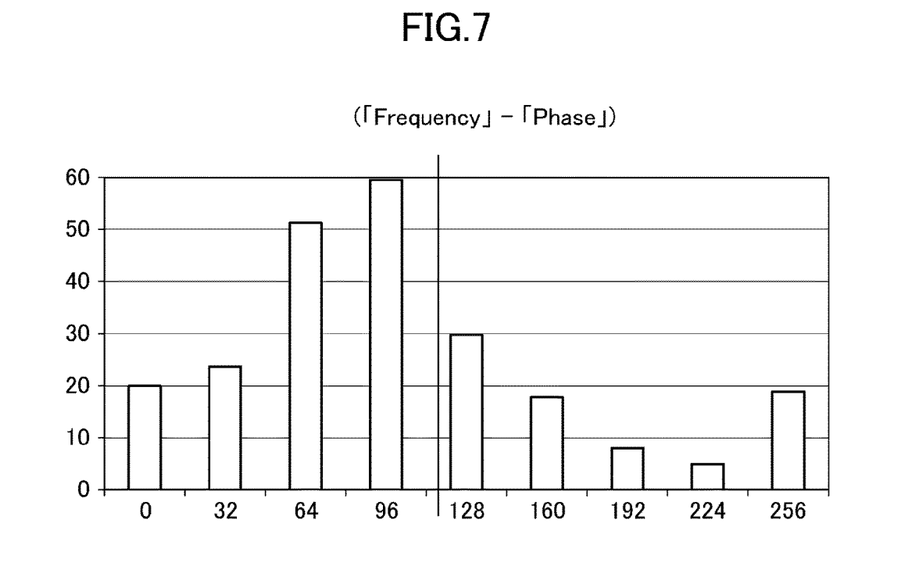
FIG. 7 is an example of a histogram of subtraction values ("Frequency"–"Phase") in a number of scan conditions actually set in the past.

FIG. 7 is an example of a histogram of subtraction values (values obtained by subtracting the values of "Phase" from the values of "Frequency") between "Frequency" and "Phase" in a number of scan conditions actually set in the past. In the histogram of FIG. 7, the horizontal axis indicates the subtraction value ("Frequency"−"Phase"), and the vertical axis indicates the frequency, respectively. The width of each bin has been adjusted in such a manner that the distribution shape of the frequency often appears. In the histogram, the number of the subtraction values to be adopted is significantly reduced when the corresponding subtraction value exceeds "96" of a peak value. Therefore, for example, the threshold T is determined as "96" corresponding to the peak value.

At step S7, the determining part 102 determines the values of a band width "BW" and the number of additions "NFX", based on the set contents of the SN ratio level "SNR", the values of "Frequency" and "Phase" determined at step S6, and the set contents of "Freq. FOV", "Phase FOV" and "Slice Thickness".

Specifically, for example, a plurality of candidates are first prepared for each combination of "BW" and "NEX".

The combination of "BW" and "NEX" suitable for candidates is generally determined depending on the settings of the imaging region "Anatomy" and the scan method (data acquiring method "PStype" and contrast "Contrast"). The candidates can theoretically or experimentally be determined. Thus, specifically, for example, a plurality of candidates are determined in advance for each combination of "BW" and "NEX" for every settable combination of the imaging region "Anatomy" and the scan method (data acquiring method "PStype" and contrast "Contrast"). They are prepared in a table. Then, a plurality of candidates corresponding to the actual set contents of the imaging region "Anatomy" and the scan method (data acquiring method "PStype" and contrast "Contrast") are read referring to the table.

A candidate determining method based on statistics will now be described as one example of a method for determining a plurality of candidates with respect to the combination of "BW" and "NEX" for every settable combination of the imaging region "Anatomy" and the scan method (data acquiring method "PStype" and contrast "Contrast"). This method is used to determine appropriate candidates by utilizing a number of scan conditions actually set in the past as teacher data.

Figure 8:
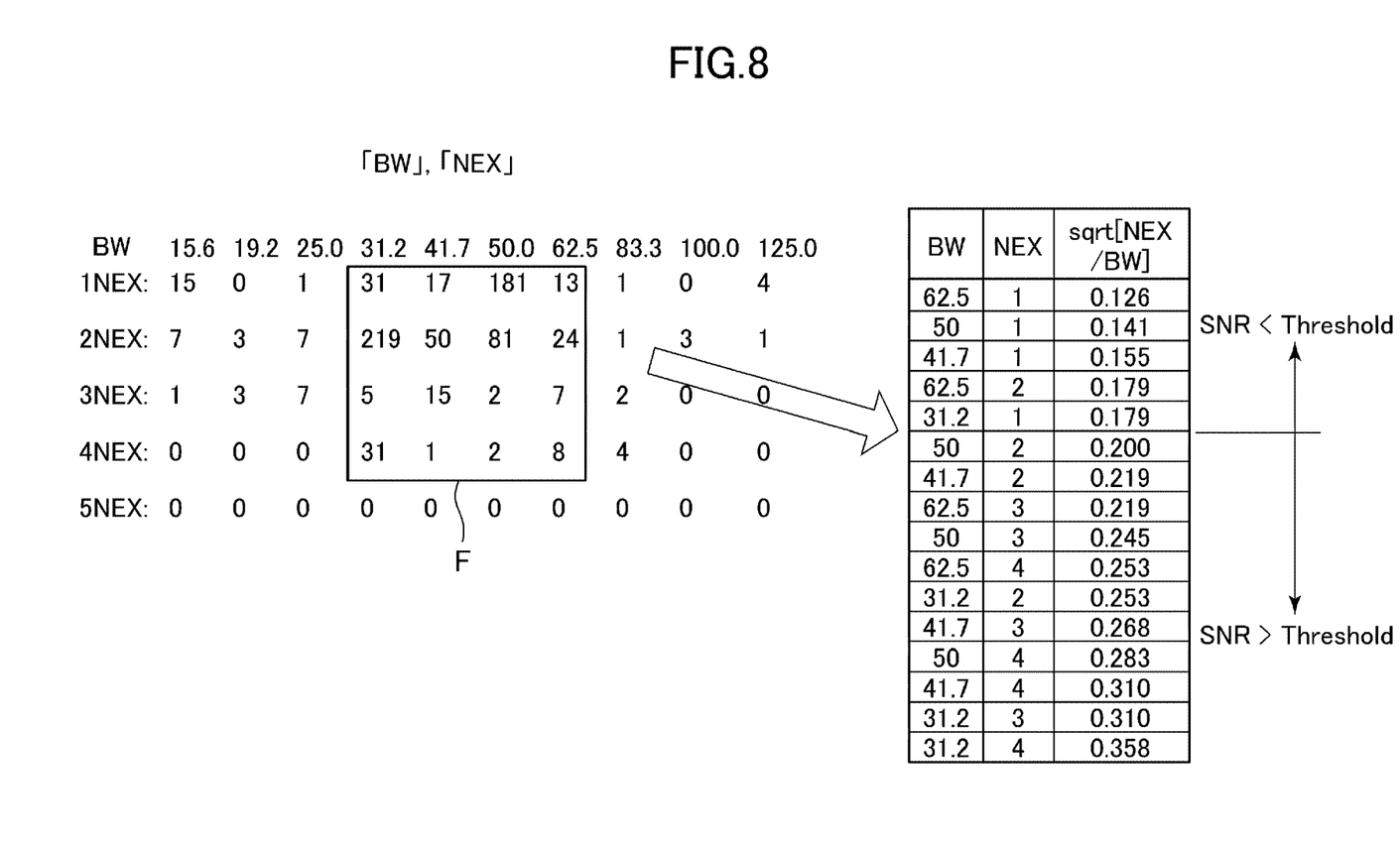
FIG. 8 is an example of a 2D (Dimension) histogram of combinations of "BW" and "NEX" in a number of scan conditions actually set in the past.

FIG. 8 is an example of a 2D histogram of combinations of "BW" and "NFX" in a number of scan conditions actually set in the past. In FIG. 8, the horizontal axis indicates the value of a band width "BW", and the vertical axis indicates the value of the number of additions "NEX". Values at coordinates corresponding to the combination of these indicate frequencies. In the example of FIG. 8, the set contents of the imaging region "Anatomy" and the scan method (data acquiring method "PStype" and contrast "Contrast") have been narrowed down under the condition of being "Brain", "FSE" and "T2".

Incidentally, "BW" has the property that when it is excessively small, a chemical shift occurs so that image quality is deteriorated, whereas when it is excessively large, the SN ratio is degraded. "NEX" has the property that when it is excessively large, a scan time becomes long.

As can be seen from the 2D histogram, it is understood that the combinations of "BW" and "NEX" are set to substantially avoid a range in which "BW" becomes excessively large and small, and a range in which "NEX" becomes excessively large.

Thus, for example, a rectangular frame F is set to the 2D histogram. The rectangular frame F is set to include a combination highest in frequency and eliminate the range in which "BW" becomes excessively large and small, and the range in which "NEX" becomes excessively large. A plurality of candidates for the combinations of "BW" and "NEX" when the imaging region "Anatomy" and the scan method (data acquiring method "PStype" and contrast "Contrast") are "Brain", "FSE" and "T2" are determined for the combinations included in the rectangular frame F.

Incidentally, as another method, higher prescribed numbers may be determined as the plural candidates in the order of higher frequency (in a popular order) while eliminating the range in which "BW" becomes excessively large and small, and the range in which "NEX" becomes excessively large in the 2D histogram.

Subsequently, a determination similar to the above is performed for each settable combination of the imaging region "Anatomy" and the scan method (data acquiring method "PStype" and contrast "Contrast").

A plurality of candidates are prepared for the combinations of "BW" and "NEX", and then for each candidate, an SN ratio at the time of adoption of the candidate is estimated. Incidentally, the SN ratio can be defined as follows:

$$SN \text{ ratio} = C \times \text{"Freq.FOV"} \times \text{"Phase FOV"} \times \quad (4)$$
$$\text{"Slice Thickness"} \times SQR(\text{"NEX"} \times \text{"pFOV.R"})/SQR$$
$$((\text{"Frequency"} \times \text{"Phase"} \times \text{"BW"}))$$
$$= C \times A \times SQR(\text{"NEX"}/\text{"BW"})$$

where:
SQR: square root,
"pFOV.R": "Phase FOV"/"Freq/FOV",
A: known constant, and
C: constant dependent on "Coil", "TR", "TE", etc.

Then, candidates are extracted in each of which the estimation value of the SN ratio is greater than or equal to an SN ratio corresponding to the set level of the SN ratio level "SNR" or larger than the corresponding SN ratio. In FIG. 8, an index value SQR {"NEX"/"BW"} indicative of the relative size of the SN ratio is calculated with respect to each of candidates for a plurality of combinations of "BW" and "NEX" in the rectangular frame F. The respective candidates of which index values have been arranged in ascending order thereof are indicated by an arrow. Here, SQR { } means the square root. The index value for the SN ratio corresponding to the set level of the SN ratio level "SNR" is taken to be a threshold, and each candidate can be extracted by determination of the threshold.

After the candidates have been extracted, a scan time is estimated for each of the extracted candidates Finally, the candidate in which the estimated value of scan time becomes minimal is adopted out of the extracted candidates.

At step S8, the determining part 102 determines the values of the remaining parameters needed to be set on the basis of the set contents of "Frequency", "Phase", "BW" and "NEX" determined at steps S6 and S7. The remaining parameters however differ depending on the data acquiring method (pulse sequence) "PStype" to be used. A method used best as the data acquiring method is an FSE method (except for an FLAIR method). Therefore, a description will now be made, as one example, of the case where the FSE method (except for the FLAIR method) is used as the data acquiring method.

When the data acquiring method is of the FSE method (except for the FLAIR method), the remaining parameters needed to be set are an echo train length "ETL", a repetition time "TR" and the number of measurements "#Acq".

First, one or more candidates for the value of "ETL" are determined using an "Auto ETL" function.

"ETL" is a parameter needed when the data acquiring method is of the FSE method. "ETL" has the property that when its value is increased, "DAT (Data Acquisition Time)" is eventually elongated so that a scan time becomes short, but the increase in the value causes degradation of image quality (blurring in image). Thus, a range (upper and lower limit values) suitable as a range for the value of "DAT" is determined in advance. The value of "ETL" is adjusted in such a manner that the value of "DAT" falls within the suitable range from the following relational equations.

$$\text{"DAT"} = \text{"Echo Space"} \times \text{"ETL"} \quad (5)$$

$$\text{"Echo Space"} = f(\text{"Frequency"}, \text{"BW"}) \quad (6)$$

where the values of "Frequency" and "BW" have already been determined. f( ) indicates the function.

Next, the values of "TR" and "#Acq" are automatically determined for each candidate for the value of "ETL" using an "Auto TR" function. "TR" is a parameter always needed regardless of the data acquiring method, but the value thereof may be fixed without causing the operator to allow settings as the case may be. "#Acq" is a parameter that has a large effect on the scan time. If the number of slices of an image to be acquired is up to a prescribed value N (30, for example), "#Acq" becomes 1, if the number of the slices thereof is up to a prescribed value N×2, "#Acq" becomes 2, and so on. The scan time has the property of substantially linearly increasing with the value of "#Acq". The "Auto TR" function is the function of optimizing "TR" and "#Acq", based on "ETL" in such a manner that the scan time becomes minimal, and is of the existing technique.

Then, candidates for a combination minimized in scan time are adopted out of the candidates for the combinations of "ETL", "TR" and "#Acq".

At step S9, the determined values of "Frequency", "Phase", "NEX", "BW", "ETL", "TR" and "#Acq" are displayed. The estimated scan time is also displayed.

At step S10, a command for determining a scan condition and a parameter's setting change are accepted.

At step S11, it is determined whether any parameter has been changed. If the change in the parameter is made, the processing returns to step S2, when the determination of each parameter is performed again. On the other hand, when the change is not made, the processing proceeds to step S12.

At step S12, it is determined whether the scan condition determination command has been done. When the scan condition determination command is determined not to have been done, the processing returns to step S10. On the other hand, when the scan condition determination command is determined to have been done, the scan condition is established and the processing is ended.

According to the present embodiment such as described above, the matrix number in the frequency encode direction and the matrix number in the phase encode direction both related to the generated image are determined based on the set imaging coverage and desired spatial resolution. The band width and the number of additions are determined based on the determined two matrix numbers, the set imaging coverage and the set desired SN ratio. It is therefore possible to begin with the parameters to which the operator pays attention and to automatically determine such individual physical parameters as to satisfy the parameters, thereby making it possible to more conveniently perform the optimization of the scan conditions in the magnetic resonance imaging system. Since the method for determining the individual parameters is simple, it is advantageous in the development cost of algorithm, the time required for the optimization processing, stability with respect to the adequacy of the determined parameters, and the like.

In the present embodiment as well, the scan conditions actually set in the past have been utilized as the teacher data in determining the parameter's set range and candidates. It is therefore possible to reflect the criteria on the parameter settings that the operator has acquired experimentally, on the parameter determining method and to reasonably determine, with a simple method, many parameters that interact with each other complicatedly.

Incidentally, the invention is not limited to the above embodiment, but various modifications or the like can be made thereto within the scope not departing from the gist of the invention.

For example, the association between the respective levels of the spatial resolution "Resolution" and the concrete spatial resolutions, the association between the respective levels of the SN ratio "SNR" and the concrete SN ratios, the candidates for the combinations of "BW" and "NFX" and the like may be prepared for every either one of the imaging region and the scan method or for every other condition.

Further, for example, the number of slices "#Slices" may automatically be determined based on the set contents of a desired spatial resolution in a z-axis direction and a range of an imaging region in the z-axis direction. The desired spatial resolution in the z-axis direction may be taken as the slice thickness "Slice Thickness".

Furthermore, for example, the scan conditions actually set in the past, which are used as the teacher data, may be targeted for all worldwide-scale data, but may be limited to those set by veteran engineers that have predetermined years of experience or more. Alternatively, since the skills of engineers are considered to differ for each country or region, the scan conditions may be limited to those set in countries or regions when the skills of the engineers are considered to be high. Or more specifically, since the physiques of subjects are considered to differ for each country or region, the scan conditions may be limited to those set in the same countries or regions as those when a magnetic resonance apparatus is used. In these cases, an improvement in the accuracy at the optimization of each parameter can be expected.

The present embodiment is of the magnetic resonance imaging system, but the scan condition determining method of optimizing the parameters as described above, a scan condition determining device for executing this method, a program for allowing a computer to function as the scan condition determining device, a storage medium storing the program therein, and the like are also each an embodiment of the present invention.

Many widely different embodiments of the invention may be configured without departing from the spirit and the scope of the present invention. It should be understood that the present invention is not limited to the specific embodiments described in the specification, except as defined in the appended claims.

The present invention is applied to the apparatus which begins with parameters to which an operator pays attention and which automatically determines individual physical parameters in a magnetic resonance imaging system, and the apparatus can optimize scan conditions more conveniently.

What is claimed is:
1. A scan condition determining apparatus which determines scan conditions in a magnetic resonance imaging system, the scan condition determining apparatus comprising:
   a setting unit for receiving setting of an imaging range, a spatial resolution and a signal to noise ratio; and
   a determining unit for determining a matrix number in a frequency encode direction and a matrix number in a phase encode direction, based on the imaging range and the spatial resolution set by the setting unit and determining physical parameters different from the matrix number in the frequency encode direction and the matrix number in the phase encode direction, based on the determined matrix numbers, the set imaging range and the set signal to noise ratio,
   wherein the determining unit determines the matrix number in the frequency encode direction and the matrix number in the phase encode direction in such a manner that a value obtained by subtracting the matrix number in the phase encode direction from the matrix number in the frequency encode direction is less than a predetermined value.

2. The scan condition determining apparatus according to claim 1, wherein the setting unit prepares a plurality of spatial resolutions as choices for an operator to select according to set contents of an imaging region and/or a scan method by referring to a pre-determined table.

3. The scan condition determining apparatus according to claim 2, wherein a most frequently used spatial resolution historically is at a center of the plurality of spatial resolutions as choices.

4. The scan condition determining apparatus according to claim 1, wherein the setting unit prepares a plurality of signal to noise ratios as choices for an operator to select according to set contents of an imaging region and/or a scan method by referring to a pre-determined table.

5. The scan condition determining apparatus according to claim 4, wherein the plurality of signal to noise ratios as choices are in a range of signal to noise ratios used historically.

6. The scan condition determining apparatus according to claim 1, wherein the image range is a field of view area.

7. The scan condition determining device according to claim 1, wherein the predetermined value is a historically most often occurred difference between the matrix number in the frequency encode direction and the matrix number in the phase encode direction.

8. The scan condition determining device according to claim 1, wherein the physical parameters include at least one of a band width and the number of excitations.

9. The scan condition determining apparatus according to claim 8, wherein the determining unit prepares a plurality of combinations each based on a band width and the number of excitations as choices for an operator to select according to set contents of an imaging region and/or a scan method by referring to a pre-determined table, and determines the band width and the number of excitations by adopting a combination in which a signal to noise ratio estimated upon adoption of the each combination among the plurality of combinations becomes more than the signal to noise ratio and in which a scan time estimated upon the combination adoption there among becomes minimal.

10. The scan condition determining apparatus according to claim 8, wherein the determining unit determines the band width and the number of excitations and further determines an echo train length, based on the determined matrix number in the frequency encode direction, matrix number in the phase encode direction, band width and number of additions, and set contents of a data acquiring method.

11. A magnetic resonance imaging system including a scan condition determining apparatus, the scan condition determining apparatus comprising:
   a setting unit for receiving setting of an imaging range, a spatial resolution and a signal to noise ratio; and
   a determining unit for determining a matrix number in a frequency encode direction and a matrix number in a phase encode direction, based on the imaging range and the spatial resolution set by the setting unit and determining physical parameters different from the matrix number in the frequency encode direction and the matrix number in the phase encode direction, based on the determined matrix numbers, the set imaging range and the set signal to noise ratio,
   wherein the determining unit determines the matrix number in the frequency encode direction and the matrix number in the phase encode direction in such a manner that a value obtained by subtracting the matrix number in the phase encode direction from the matrix number in the frequency encode direction is less than a predetermined value.

12. A scan condition determining method for determining scan conditions in a magnetic resonance imaging system, the scan condition determining method comprising the steps of:

receiving, by the magnetic resonance imaging system, setting of an imaging range, a spatial resolution and a signal to noise ratio; and determining, by the magnetic resonance imaging system, a matrix number in a frequency encode direction and a matrix number in a phase encode direction, based on the imaging range and the spatial resolution and determining physical parameters different from the matrix number in the frequency encode direction and the matrix number in the phase encode direction, based on the determined matrix numbers, the set imaging range and the signal to noise ratio, wherein the matrix number in the frequency encode direction and the matrix number in the phase encode direction are determined in such a manner that a value obtained by subtracting the matrix number in the phase encode direction from the matrix number in the frequency encode direction becomes less than a predetermined value.

13. The scan condition determining method according to claim 12, wherein the physical parameters include at least one of a band width and the number of excitations.

14. The scan condition determining method according to claim 13, wherein in the determining step, an echo train length is determined based on the determined matrix number in the frequency encode direction, matrix number in the phase encode direction, band width and number of excitations, and set contents of a data acquiring method.

* * * * *